United States Patent [19]

Richard

[11] 4,287,763
[45] Sep. 8, 1981

[54] APPARATUS FOR CONCENTRATING AND SAMPLING SUBSTANCES FROM SEAWATER

[76] Inventor: Joseph D. Richard, 5590 SW. 78 St., Apt. A, Miami, Fla. 33143

[21] Appl. No.: 65,907

[22] Filed: Aug. 13, 1979

[51] Int. Cl.³ .............................................. G01N 1/10
[52] U.S. Cl. .............................. 73/863.21; 73/170 A; 73/864.34
[58] Field of Search ....................... 73/425.4 R, 170 A; 43/7

[56] References Cited

U.S. PATENT DOCUMENTS

| | | | |
|---|---|---|---|
| 2,894,542 | 7/1959 | Alm | 73/421 R X |
| 3,310,984 | 3/1967 | Swanson | 73/421 R |
| 3,339,417 | 9/1967 | Richard | 73/425.4 |
| 3,412,612 | 11/1968 | Carr | 73/425.4 R X |
| 3,466,782 | 9/1969 | Stuart, Jr. | 73/421 R X |
| 3,589,197 | 6/1971 | Brooks, Sr. | 73/421 R |
| 3,900,982 | 8/1975 | Gale | 43/7 |
| 3,924,471 | 12/1975 | Singer | 73/421 B |
| 4,089,209 | 5/1978 | Grana et al. | 73/425.4 R X |
| 4,128,476 | 12/1978 | Rock | 210/138 X |

Primary Examiner—Daniel M. Yasich

[57] ABSTRACT

Apparatus for obtaining a series of concentrated samples of dissolved, particulate or emulsified substances from seawater. A relatively large measured volume of seawater is pumped through each of a series of in situ sampling chambers containing filtration, adsorption, absorption, or other retentive material. The instrumented housing with appended sampling chambers is preferably suspended from a surface vessel by an electrical cable through which it is remotely controlled and powered to obtain measured samples at various depths. Alternatively, a programmed controller and battery power pack can be attached to obtain an unattended time series of samples from a fixed location either on the sea floor or suspended beneath a buoy.

9 Claims, 8 Drawing Figures

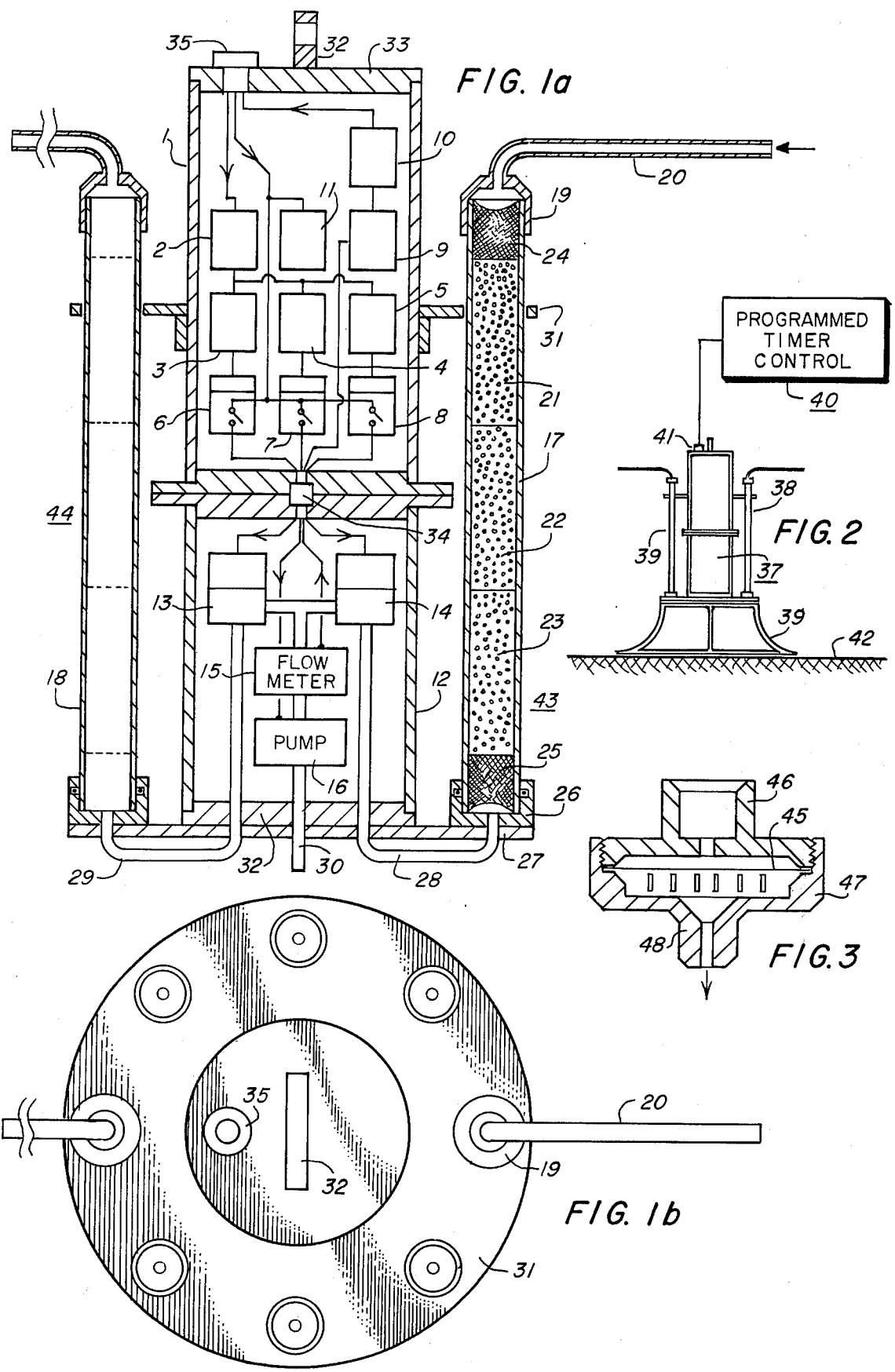

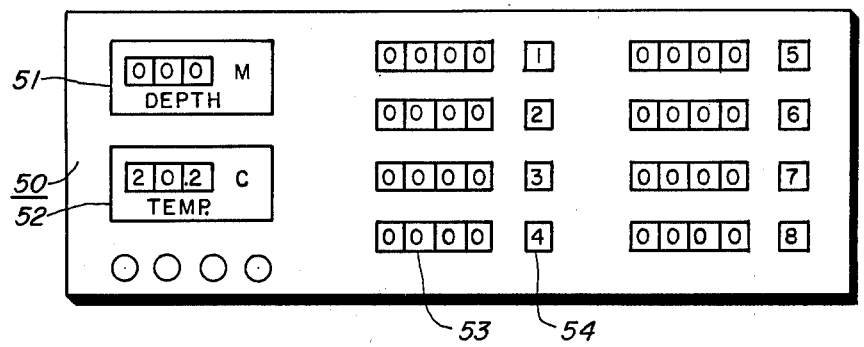
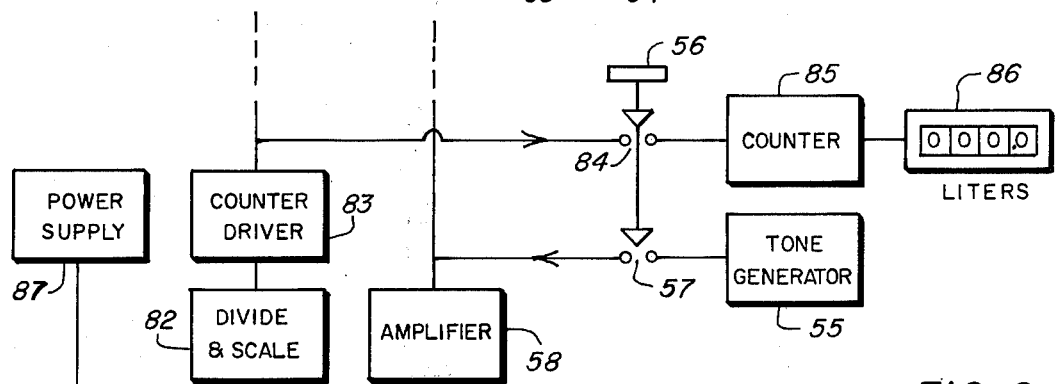
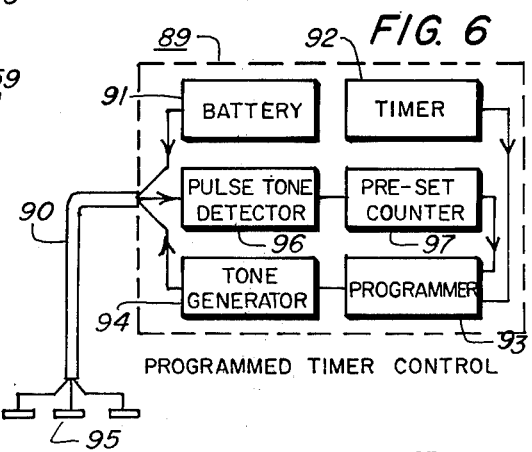
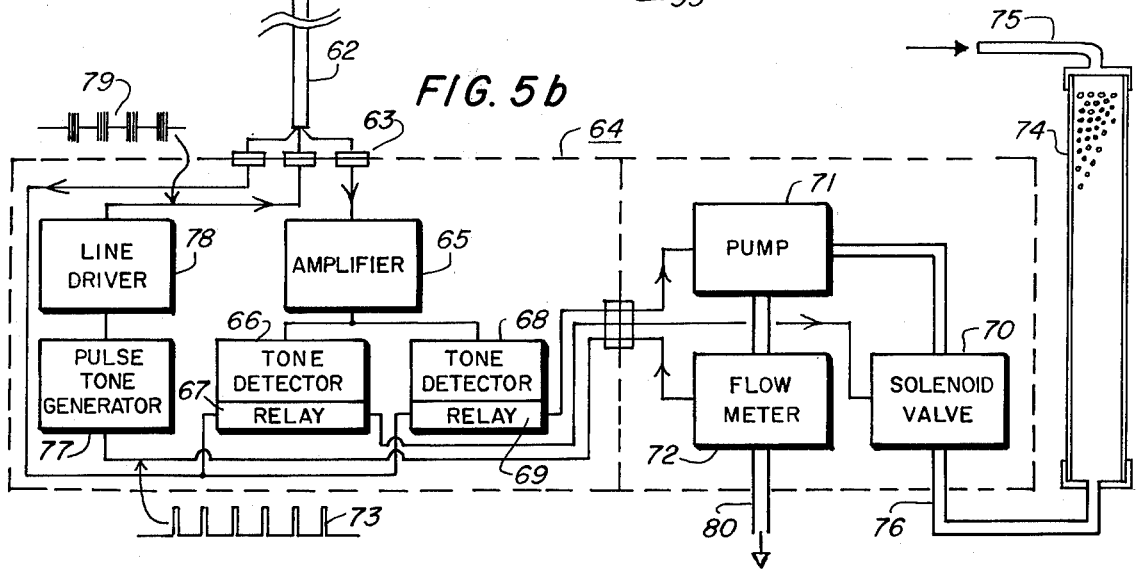

APPARATUS FOR CONCENTRATING AND SAMPLING SUBSTANCES FROM SEAWATER

BACKGROUND OF THE INVENTION

In oceanographic research it is frequently necessary to obtain samples of water from a series of discrete depths in the ocean. For certain other purposes it is desirable to obtain a series of water samples at discrete time intervals from a fixed location. Where relatively gross characteristics of the water are to be measured or analyzed, such as salinity or dissolved oxygen, a relatively small sample volume has been adequate, and a variety of simple and efficient sampling apparatus have been available for such purposes.

However, where relatively more dilute substances are being sampled for analysis or study, such as dissolved organic matter, trace elements, suspended particles, or chemical pollutants, an inconveniently large volume of water needs to be collected before an adequate sample can be filtered out or otherwise extracted.

Apparatus has been developed in the past for obtaining large volume water samples for shipboard extraction, but the methods used have been tedious or even dangerous in rough weather. As an alternative to large volume water filled bottles or bags, various pumping methods have been devised in the past for bringing aboard relatively large water samples. Generally, such methods have consisted of shipboard pump and extraction systems and a intake tube extending down to the desired sampling depth. Where a single large volume sample of water is needed from near the surface, and where sampling tube contamination from previous sampling is unimportant, a simple pumping system has been satisfactory. However, where a series of samples are needed, either at various depths or spaced at intervals over a period of time, and where contamination must be avoided, the shipboard pump with single intake tube and extraction system is not suitable.

SUMMARY OF THE INVENTION

The present invention provides a method and apparatus for extracting and concentrating a series of uncontaminated samples of various trace substances from seawater. A series of sampling chambers are arrayed around a waterproof instrumented housing. A single pump and flowmeter, and a series of solenoid valves within the housing, allow a measured volume of water to be pumped through any selected solenoid valve and its corresponding sampling chamber. In a preferred use, the sampling apparatus is suspended beneath a ship by an electrical cable so that the pump control and solenoid valve selection can be operated from above the surface. Furthermore, output signals from the flowmeter are indicated above the surface so that the volume of water pumped through each of the sampling chambers can be separately totalized and recorded.

Depending on the substances to be concentrated and sampled, various filtrating, adsorptive or other retentive material is placed in the sampling chambers. For example: one or more millipore filters may be used to concentrate and sample very small suspended particles; chelating resins may be used to concentrate certain trace elements; Amberlite (XAD) resins may be used to concentrate certain chlorinated hydrocarbons; or a fine netting material in an enlarged sampling chamber can be used to concentrate small planktonic organisms.

In a typical application, the present invention provides a plurality of expendable sampling columns, each with an individual expendable intake tube, to facilitate sequential in-situ sampling. Non-expendable components of the sampling system, including individual solenoid valves and common pump and flowmeter, are all confined to the outlet end of the sampling column. In this way, sample contamination is minimized. In a preferred use, distilled water, or other suitable liquid, is drawn into each sampling column before use to minimize the premature intrusion of seawater after immersion in the ocean.

In one preferred configuration, the present invention provides a method and apparatus for obtaining a series of concentrated samples of trace substances from various depths in the ocean. The sampling apparatus can be lowered into the ocean by means of an electrical cable so that the control and metering functions can be carried out remotely from shipboard. In another configuration, the present invention provides similar apparatus for obtaining a time series of concentrated samples of trace substances from seawater from a fixed location on the sea bottom.

BRIEF DESCRIPTION OF THE DRAWINGS

FIG. 1a is a sectioned view of sampling apparatus according to the present invention wherein eight sampling chambers are deployed around an instrumented underwater housing. As an operable illustration of the present invention, only two sampling chambers are shown in FIG. 1a. Normally closed solenoid valves are shown for each sampling chamber, and all solenoid valves feed into a single pump and flowmeter.

FIG. 1b is a top view of the sampling apparatus shown in FIG. 1a. As an operable illustration of the present invention, only two of the sampling chambers in FIG. 1b are shown with removable intake tubes attached.

FIG. 2 is a schematic view of sampling apparatus according to the present invention mounted on the sea floor to obtain a time series of concentrated samples from a fixed location.

FIG. 3 is a disk filter holder for concentrating and sampling suspended particles. One or more such disk holders can be used in place of the sampling chambers shown in FIG. 1a.

FIG. 4 shows a shipboard control panel with individual digital counters for indicating the volume of water pumped through each sampling chamber.

FIG. 5a is a block diagram of the shipboard control and metering portion of sampling apparatus according to the present invention.

FIG. 5b is a block diagram showing the operation of sampling apparatus according to the present invention. For illustrative purposes, the control operation for only one sampling chamber is shown along with the pump control and the means for transmitting the flow meter signal to the shipboard indicator.

FIG. 6 is a block diagram of a programmed timer control for use in place of the shipboard control of FIG. 5a for obtaining a time series of concentrated samples from a fixed location such as the sea floor.

DESCRIPTION OF THE PREFERRED EMBODIMENT

In FIG. 1a, an underwater housing is shown in sectional view comprising an upper cylinder 1 with sealed end-cap 33 and a lower cylinder 12 with sealed end-cap 32. As an operable illustration, only two sampling chambers 43 and 44 are shown. A waterproof electrical connector 35 allows remote control and metering of the sampling apparatus through a control cable mechanically attachable to the fitting 32. Control signals consisting of discrete tones are received from above the surface, or from the programmed timer control 40 of FIG. 2, and are conditioned by the amplifier 2. Specific tone signals are detected by corresponding tone detectors such as the tone detector 4 for controlling the pump 16 through the relay 7, and the tone detectors 3 and 5 for controlling the normally closed solenoid valves 13 and 14 through the relays 6 and 8 respectively. As only two sampling chambers are shown for purposes of illustration, only two solenoid valve control tone detectors 3 and 5, associated relays 6 and 8, and normally closed solenoid valves 13 and 14 are shown in the section view of FIG. 1a. However, it should be understood that a separate tone detector, relay, and normally closed solenoid valve is used for each sampling chamber, such as the sampling chamber 43. Electrical conductors pass between upper and lower chambers of the underwater housing through the electrical connector 34. In the schematic diagrams of FIGS. 1a, 5a, 5b, and 6, the arrows show the direction of tone signaling and they also show the flow of electrical power, such as, for example, to open solenoid valves and to activate the pump.

When the appropriate tone is detected by the tone detector 5 so that the normally closed solenoid valve 14 is opened, and the pump 16 is started by activation of the tone detector 4, water is drawn into the inlet conduit 20 through the sampling chamber 43, through the outlet conduit 28, and ejected out the exit tube 30. The flowmeter 15 generates a series of electrical pulses indicative of the volume of water passed. Each flowmeter pulse triggers a pulsed tone from the pulse tone generator 9 which is amplified by the line driver 10 for transmission to the shipboard control and metering portion of the sampling apparatus.

The first sampling chamber of FIG. 1a comprises a tube 17 slip fitted into an O-ring sealed socket 26 mounted on the base plate 27. The upper end of the sampling chamber is supported by the collar 31. Three sections of adsorbent material 21, 22, and 23 are shown within the tube 17. Porous plugs 24 and 25 confine the adsorbent material within the tube 17. The inlet conduit 20 is attached to the upper end of the sampling chamber 43 by means of the cap fitting 19. On the opposite side of the sampling apparatus, the outlet conduit 29 connects the sampling chamber 44 with the solenoid valve 13. As shown in FIG. 1b, eight sampling chambers can be arrayed around the central control housing.

In FIG. 2, sampling apparatus 37, similar to that shown in FIG. 1, is shown mounted on the base 39 resting on the sea floor 42. Sampling chambers 38 and 39 are representative of eight arrayed around the control housing. As an alternative to a shipboard control system, a programmed timer control 40 is connected to the sampling apparatus 37 by means of the waterproof cable connector 41.

FIG. 3 shows a conventional disk filter holder consisting of upper and lower threaded portions 46 and 47 which are shaped to contain and support a disk filter 45. Such disk filter holders are configured so that they may be stacked in series. The exit fitting 48 fits into the O-ring sealed socket 26 of the sampling apparatus of FIG. 1a so that a disk filter holder, or a series of such holders, can be used in place of the sampling chambers of FIG. 1.

In FIG. 4, a control and metering panel 50 is shown with an individual flowmeter totalizer for each sampling chamber of the sampling apparatus according to the present invention. For example, when the selector switch 54 is depressed, solenoid valve number 4 is opened, the pump is started, and the digital counter 53 totalizes the water volume passing through sampling chamber number 4. A depth readout 51 indicates the depth of the sampling apparatus, and the temperature readout 52 indicates the corresponding temperature.

In FIG. 5a, the tone generator 55 represents one of a series of tone generators for activating the various tone detectors in the underwater portion of the sampling apparatus shown in FIG. 5b. Although only one control tone generator and sampling chamber is shown for purposes of illustration in FIGS. 5a and 5b, it should be understood that a plurality of such tone generators are used to activate corresponding tone detectors to control a plurality of solenoid valves, each associated with a corresponding sampling chamber. A separate tone generator is used to activate the tone detector 68 which controls the sampling pump 71. For example, when the push button 56 is depressed, the switch 57 connects the tone generator 55 signal to the amplifier 58. At the same time, another switch contact (not shown), ganged with the switch contacts 57 and 84, connects the pump control tone generator to the amplifier 58. The line drive amplifier 59 output, consisting of tone signals for opening one of the solenoid valves and activating the sampling pump, is transmitted down the electrical cable 62 through the slip ring 60 of the winch 61. A shipboard power supply 87 powers the various components within the underwater portion of the sampling apparatus through the slip ring 88 and the signal cable 62.

In FIG. 5b, the underwater connector 63 connects the cable 62 into the waterproof housing 64 of the sampling apparatus. Appropriate tone signals amplified by the amplifier 65 activate the tone detector-relay 66-67 to open the normally closed solenoid valve 70 and simultaneously activate the tone detector-relay 68-69 to operate the pump 71. When the solenoid valve 70 is open and the pump 71 is operating, water is drawn into the inlet conduit 75 of the sampling chamber 74 and ejected from the exit tube 80. The flowmeter 72 generates a series of pulses 73 indicating the volume of water being drawn through the sampling chamber 74. Pulses 73 from the flowmeter trigger pulsed tones 79 from the pulse tone generator 77. Amplified pulsed tones are transmitted up the cable 62, through the slip-ring 80, to the pulse tone detector 81. Counter pulses are generated by the pulse tone detector 81 corresponding to the received pulsed tones. The counter pulses are divided and scaled by the circuit 82 so that the counter driver 83 output corresponds to suitable units of water volume measured by the flowmeter 72. For example, ten pulses from the counter driver 83 corresponds to one liter of water passing through the flowmeter 72. In this way the number of liters of water pumped through the sampling chamber 74 is counted and indicated by the digital counter 85-86. FIG. 5b is a schematic diagram to further illustrate the operation of the present invention and is not intended as an alternate view of the apparatus shown in FIG. 1a.

In FIG. 6, a programmed timer control 89 is shown which can be connected to the waterproof sampler control housing 64 by means of the connectors 95 and 63 when the shipboard control system of FIG. 5a is disconnected at the connector 63. The programmed timer control 89, powered by the battery 91, allows unattended operation of the sequential sampling process in the absence of the shipboard control and metering components of FIG. 5a. The programmed timer control 89 is used to obtain a time series of water samples from a fixed location such as on the sea bottom as shown in FIG. 2. When the programmer 93 is activated by the timer 92, signals from the tone generator 94 are transmitted to the amplifier 65 through the cable 90 and mated connectors 63 and 95. As described for the shipboard control of FIG. 5a, a specific tone activates the pumped flow through a specific sampling chamber. However, as the various sampling chambers are selected in succession over a period of time by the time control of FIG. 6, the water volume passed through each is totalized by the pre-set counter 97 until a predetermined volume has been reached. After the predetermined volume of water has been pumped through a sampling chamber as determined by the pre-set counter 97, the programmer 93 terminates the pump and solenoid valve activation signals until some later time when the timer re-initiates the process with the following sampling chamber.

From the foregoing it will be seen that the present invention provides a method and apparatus suitable for extracting and concentrating a variety of trace substances from seawater. Although one particular construction is shown in the drawings, many alternatives to the details shown are possible. For example, other signaling techniques for accomplishing the remote control and metering functions can be used as alternatives to the tone signaling method shown in the figures. As another alternative, the need for coded signaling can be eliminated altogether, if the pump and solenoid valves are controlled by selectively switching power to them down the multi-conductor cable from which the sampler is suspended. Output pulses from some types of flowmeters can be transmitted directly up a conductor of the cable without the need for the pulsed tones for carrying the information as shown in the drawings. However, where a very long suspending cable is used with only a few conductors, such as two inner conductors with an outer wrap of steel tension bearing strands, and where a plurality of solenoid valves are to be individually controlled, some form of coded signaling is preferred.

One alternative which reduces the need for multiple discrete control signals is the optional use of a single rotary-solenoid driven selector valve with multiple input conduits in place of the plurality of individual solenoid valves. A current pulse to the rotary-solenoid causes the selector valve to rotate stepwise to the next position so that the single pump-flowmeter combination is sequentially connected to each of the sampling chambers. Such stepping selector valves are commercially available. However, the use of separate solenoid valves, as shown in the drawing, is less expensive, and this has the advantage of allowing the simultaneous opening of more than one valve, or even all of the valves, where one large volume sample is needed. As a further possible alternative, the use of multiple, individually controlled pumps, with manifold input to a common flowmeter, could eliminate the need for valves altogether.

In the Figures, a separate control signal is used to operate the pump. Since pump operation is needed only when at least one of the solenoid valves is opened, an obvious alternative to the structure shown would be to eliminate the pump control signaling components and instead have the pump operate when any one of the solenoid valves is opened. In FIG. 4, separate digital indicators are shown for showing the totalized volume of seawater pumped through each sampling chamber. Obviously, a single flow totalizer could be used and re-set to zero before pumping is started through each successive sampling chamber.

The present invention provides a method and apparatus which is also suitable for concentrating and sampling planktonic organisms from oceanic or estuarine waters. For many organisms, a relatively large volume of water needs to be pumped through a filter or plankton netting before an adequate sample is accumulated. Therefore, when the apparatus of FIG. 1 is used for such purposes, relatively large diameter sampling chambers (e.g., of clear plexiglas) should be used containing a closed inner sleeve of plankton netting of slightly smaller diameter. The large surface area of plankton netting presents relatively little resistance to the pumped flow so that a much larger volume water sample is practical. A relatively larger volume pump can also be used because of the relatively low pressure drop across the plankton netting within the sampling chamber.

When only smaller particles are to be concentrated and sampled by the apparatus shown in FIG. 1, larger particles and plankton can be excluded by placing a suitable filter on the intake of the tube 20. The lower housing 12 shown in FIG. 1 can be fluid filled and a pressure equalization gland added to eliminate the need for special high pressure solenoid valves, tubing, pump and flowmeter. Immersion type pump, flowmeter, and solenoid valves can be used within the pressure equalized fluid filled lower housing. Before use of the sampling apparatus, distilled water, or other non-contaminating fluid, can be pumped into each sampling chamber to prevent the premature intrusion of seawater into the sampling chambers when the apparatus is lowered into the ocean.

Depending on the trace substances to be concentrated and sampled, various porous materials can be placed in the sampling chambers. For example, where certain chlorinated hydrocarbons are being sampled, an Amberlite (XAD) resin adsorption column might be used. The adsorption efficiency is not 100%, and it varies with the trace substance being sampled, with substrate material, porosity, surface area, and also with pumping rate. However, if sections of the adsorption column are extracted and analyzed separately, the adsorption efficiency factor can be determined. A large difference in the amount adsorbed by the first and last sections of the column indicates that the adsorption efficiency is high, whereas if there is relatively little difference between the first and last sections the adsorption efficiency is relatively low. In any event, by separately extracting and measuring the amount of trace substance concentrated by the individual sections comprising the adsorption column, for example the 3 sections shown in FIG. 1, a progression equation can be applied to determine the amount of trace material that would be adsorbed by an infinite number of such sections in series. Usually, the concentrations of chlorinated hydrocarbons found in seawater are considerably below one nanogram per liter.

As an alternative to pumping a measured predetermined volume of water through each of the sampling chambers over a variable time period, the pumping can instead be limited to a predetermined time duration for each sampling chamber. If so, the volume of water pumped through each sampling chamber needs to be measured. Where relatively large volumes of water are pumped at a high rate, such as when sampling plankton, a separate mechanical counter type flowmeter can be used to totalize the flow through the outlet conduits of each of the sampling chambers. Such mechanical counter flow meters retain their digital totalized flow indication so that they can be read after the sampling apparatus is recovered from the sea.

While the present invention has been described as a method and apparatus for concentrating and sampling trace substances from seawater, the apparatus is also suitable for sampling substances such as pollutants sometimes found in relatively great abundance. For example, the sampler is suitable for concentrating or aggregating samples of tar globules, emulsified oil, or other products of oil spills, and various other pollutants which can occur in solution or as particles, emulsions, or layered suspensions between the sea surface and the sea bottom. For certain oil products, an absorbent porous material can be used in place of adsorption or filtration material in the sampling chambers. Considerably larger diameter sampling chambers with wider inlet conduits can be used for collecting emulsified oil or suspended oil globules.

While only certain preferred embodiments are shown and described herein, it is understood that many other modifications are possible and the invention is not limited to the specific structure shown, nor otherwise, except as set forth in the following claims.

What is claimed is:

1. Apparatus for obtaining a series of concentrated samples of trace substances from seawater in selected depths in the ocean comprising:
    an instrumented body suitable for submersion in seawater; a signal cable for connecting said instrumented body with a surface vessel;
    a plurality of sampling chambers arrayed around said instrumented body, each said sampling chamber having an inlet conduit and an outlet conduit; a porous material maintained within each of said sampling chambers for retaining and concentrating at least one substance occurring in seawater;
    a plurality of electrically operated valves each for normally closing a selected one of the outlet conduits of one of said sampling chambers;
    a pump connectable to the outlet conduit of any of said sampling chambers whenever corresponding said electrically operated valve is opened;
    a flowmeter disposed to measure the seawater volume passing through a selected at least one of said sampling chambers which are open to said pump via a selected at least one of said valves;
    remote control means operable from the aforementioned surface vessel for controlling said pump and a selected at least one of said electrically operated valves; and
    remote indicating means operable adjacent said remote control means for totalizing and monitoring the volume of seawater measured by said flowmeter.

2. Apparatus as described in claim 1 wherein said porous material within said sampling chambers comprises a granular adsorption medium for retaining and concentrating at least one dissolved substance occurring in seawater passed through said sampling chambers.

3. Apparatus as described in claim 1 wherein said porous material within said sampling chambers comprises at least one filtration member for retaining and concentrating particulate matter from seawater passed through said sampling chambers.

4. Apparatus as described in claim 1 wherein said porous material within said sampling chambers comprises an absorption medium for retaining and concentrating chemical pollutants from seawater passed through said sampling chambers.

5. Apparatus for obtaining a series of concentrated samples of trace substances from seawater in selected depths in the ocean comprising:
    an instrumented housing suitable for submersion in seawater;
    a source of electrical power for said instrumented housing;
    a plurality of sampling chambers connected to said housing, each said sampling chamber having an inlet conduit and an outlet conduit;
    porous material maintained within each said sampling chamber for retaining and concentrating at least one substance occurring in seawater passed through said chambers;
    means for selectively positioning said instrumented housing beneath the sea surface;
    a plurality of electrically operated valves each for normally closing a selected one of the outlet conduits of one of said sampling chambers;
    a pump connectable to the outlet conduit of any of said sampling chambers whenever corresponding said electrically operated valve is opened;
    flow measuring means arranged and disposed to measure the seawater pumped through a selected at least one of said sampling chambers which are open to said pump via a selected at least one of said valves;
    timing and control means for controlling said pump and a selected at least one of said electrically operated valves so that seawater is sequentially pumped through said sampling chambers each at a predetermined different time;
    means for totalizing the output of said flow measuring means when seawater is pumped through each of said sampling chambers; and
    control means for terminating said pump and closing the said electrically operated valves after a measured seawater sample has been pumped through said sampling chambers.

6. Apparatus as described in claim 5 wherein said means for positioning said sampling chambers beneath the sea surface comprises a base structure for mounting the sampling apparatus on the sea bottom.

7. Apparatus as described in claim 5 wherein said means for totalizing the output of said flow measuring means activates said control means for terminating said pump and closing said electrically operated valves after a predetermined seawater volume has been pumped through said sampling chambers.

8. Apparatus as described in claim 5 wherein said timing and control means for controlling said pump and said electrically operated valves sequentially pump seawater though said sampling chambers each beginning at a predetermined different time; and said control means for terminating said pump and closing said electrically operated valves terminates said pump and closes said electrically operated valves after a predetermined pumping time duration for each of said sampling chambers.

9. Apparatus as described in claim 5 wherein said porous material within each of said sampling chambers comprises an absorption medium for retaining and concentrating chemical pollutants from seawater passed through said sampling chambers.

* * * * *